US009358151B2

(12) United States Patent
Peardon

(10) Patent No.: US 9,358,151 B2
(45) Date of Patent: Jun. 7, 2016

(54) THERAPEUTIC COOLING PILLOW

(76) Inventor: Nancy Kathleen Peardon, Tarzana, CA (US)

( * ) Notice: Subject to any disclaimer, the term of this patent is extended or adjusted under 35 U.S.C. 154(b) by 334 days.

(21) Appl. No.: 13/604,828

(22) Filed: Sep. 6, 2012

(65) Prior Publication Data

US 2013/0066408 A1    Mar. 14, 2013

Related U.S. Application Data

(60) Provisional application No. 61/532,280, filed on Sep. 8, 2011.

(51) Int. Cl.
*A61F 7/02* (2006.01)
*A61F 7/00* (2006.01)
*A61F 7/10* (2006.01)

(52) U.S. Cl.
CPC .......... *A61F 7/02* (2013.01); *A61F 2007/0011* (2013.01); *A61F 2007/0207* (2013.01); *A61F 2007/0223* (2013.01); *A61F 2007/108* (2013.01)

(58) Field of Classification Search
CPC ............... A61F 2007/0001; A61F 2007/0012; A61F 2007/108; A61F 2007/0207; A61F 2007/0223; A61F 7/02; A61F 7/10; A61F 7/086; A61F 2007/0231; A61F 2007/0011
USPC ........... 5/636, 641, 644, 654, 655.4; 607/108, 607/109; 2/207
See application file for complete search history.

(56) References Cited

U.S. PATENT DOCUMENTS

| | | | | |
|---|---|---|---|---|
| 5,072,598 A | * | 12/1991 | Dibrell | A41D 13/0055 2/91 |
| 5,375,278 A | * | 12/1994 | VanWinkle et al. | 5/644 |
| 5,445,349 A | * | 8/1995 | Hart | 248/118 |
| 5,545,199 A | | 8/1996 | Hudson | |
| 5,584,086 A | * | 12/1996 | VanWinkle et al. | 5/644 |
| 5,603,727 A | * | 2/1997 | Clark et al. | 607/108 |
| 5,628,772 A | * | 5/1997 | Russell | 607/109 |
| 5,956,963 A | | 9/1999 | Lerner | |
| 5,996,152 A | * | 12/1999 | Wilson | 5/655 |
| 2002/0052566 A1 | * | 5/2002 | Sequeira | A61F 7/02 601/112 |
| 2002/0198580 A1 | * | 12/2002 | Clayton | 607/109 |
| 2003/0167556 A1 | * | 9/2003 | Kelley | 2/206 |
| 2004/0243203 A1 | * | 12/2004 | Lavine | 607/114 |
| 2005/0101220 A1 | * | 5/2005 | Jackson | 446/369 |
| 2007/0151261 A1 | * | 7/2007 | Roberts | F25D 5/02 62/4 |
| 2008/0066233 A1 | * | 3/2008 | Russell | 5/632 |
| 2008/0108986 A1 | * | 5/2008 | Meneses | 606/28 |
| 2008/0200971 A1 | * | 8/2008 | Dodo | 607/108 |
| 2008/0208299 A1 | * | 8/2008 | Martineau | 607/112 |
| 2009/0036960 A1 | * | 2/2009 | Blair | 607/109 |
| 2010/0198323 A1 | * | 8/2010 | Jung | 607/109 |
| 2011/0301675 A1 | * | 12/2011 | Mizrahi | 607/114 |

OTHER PUBLICATIONS

Website http://www.kaboodle.com/reviews/herbal-works-stress-and-pain-rescue-kit.

* cited by examiner

*Primary Examiner* — Kaitlyn Smith
*Assistant Examiner* — Yasamin Ekrami
(74) *Attorney, Agent, or Firm* — Berliner Steffin Azod LLP

(57) ABSTRACT

An apparatus and method of relieving hot flashes or body overheating or insomnia by applying to the body of a person in need of relief therefrom a cooled elongate flexible pillow filled with pellets having sufficient weight and flow properties to provide a comforting wrapping effect on the back of the neck. A preferred filler is wheat berries. In a particular embodiment, the pillow is draped over the stellate-ganglion area of the neck.

4 Claims, 5 Drawing Sheets

THERAPEUTIC COOLING PILLOW

CROSS-REFERENCE TO RELATED APPLICATIONS

This application claims the benefit of Provisional Patent Application No. 61/532,280, filed Sep. 8, 2011.

FIELD OF THE INVENTION

The present invention generally relates to therapeutic devices and the like and methods for providing comfort from and in mitigating the effects of hot flashes caused by the hormonal changes brought about by menopause and perimenopause.

BACKGROUND OF THE INVENTION

It is well known that hot flashes are a common symptom of menopause and hot flash manifestations are suffered predominantly by women. Hot flashes are also a common side effect from the use of such pharmaceutical compounds as Tamoxifen, or other aromatase inhibitors. Men have also reported hot flashes as a result of their treatment for certain forms of cancer. There are pharmaceutical treatments, injected or taken orally, and herbal remedies and the like, available to fend off the discomfort of hot flashes. U.S. Pat. No. 5,956,963 describes a wrist cooler which the inventor contends offers relief for hot flash symptoms of menopause and body overheating. The wrist cooler includes pellets that are broken to provide cooling in a one-time use manner. U.S. Pat. No. 5,545,199 describes a hot and cold therapeutic pillow that contains a gel pack that may be heated in a microwave oven or cooled by freezing.

It is also known to block the stellate-ganglion by injecting a local anesthetic in the sympathetic nerve tissue of the neck to reduce the number of hot flashes and night awakenings suffered by breast cancer survivors and women experiencing extreme menopause. The stellate ganglion (or cervicothoracic ganglion or inferior cervical ganglion) is a sympathetic ganglion formed by the fusion of the inferior cervical ganglion and the first thoracic ganglion, located at the level of the C7 (7th cervical vertebrae), anterior to the transverse process of C7, anterior to the neck of the first rib, and just below the subclavian artery. Such treatments require clinical procedures.

BRIEF SUMMARY OF THE INVENTION

The present invention overcomes the foregoing drawbacks by providing a reusable therapeutic cooling pillow that can be applied to the body of a person in need of relief from hot flashes or body overheating or insomnia. Insomnia is one of the key symptoms of overheating. The apparatus can be applied around the neck area works to reset the body's thermostat naturally, via chilling the Stellate Ganglion, which, in turn, quells hot flashes, night sweats, and relieves insomnia because cooling the brain induces sleep. In its broader application, the apparatus can be applied to any part of the body where icing is desired, (for example by wrapping it around the hand, foot, or knee, to treat a burn or an athletic injury) because the chill it provides is uniform, lengthy, and dry, maintaining maximum cold for thirty minutes.

In a particular embodiment, the apparatus drapes over the stellate-ganglion area of the neck to relieve hot flashes, body overheating or insomnia. Of significant importance, solid pellets are used as filler for the pillow, the pellets having sufficient weight and flow properties to provide a comforting wrapping effect on the back of the neck. In a specific important embodiment of the invention, the pillow is filled with raw, natural whole grains composed of its bran, germ, and endosperm. In its most advantageous form, the pillow is filled with reddish, natural wheat berries (also referred to as wheatberries), which the inventor has found to provide the unique ability to be easily cooled in the freezer compartment of a refrigerator, but which when applied over the back side of the neck of a user retains its coolness for a time sufficient to provide the desired relief.

In a further embodiment of the invention, the pillow comprises an inner elongate sleeve, closed at one end and open at the other end to receive the pellets. It is preferably of muslin, such as is formed from unbleached or white cloth produced form carded cotton yarn. The inner sleeve is filled with the solid pellets, and then closed, e. g., with opposing Velcro strips sewn to the inner surfaces of the open end of the inner sleeve. The inner sleeve is inserted into an outer sleeve of about the same size of soft cotton and can bear a decorative design. It also is closed at one end and open at the other end to receive the inner sleeve, then also closed with opposing Velcro strips sewn to the inner surfaces of the open end of the outer sleeve.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
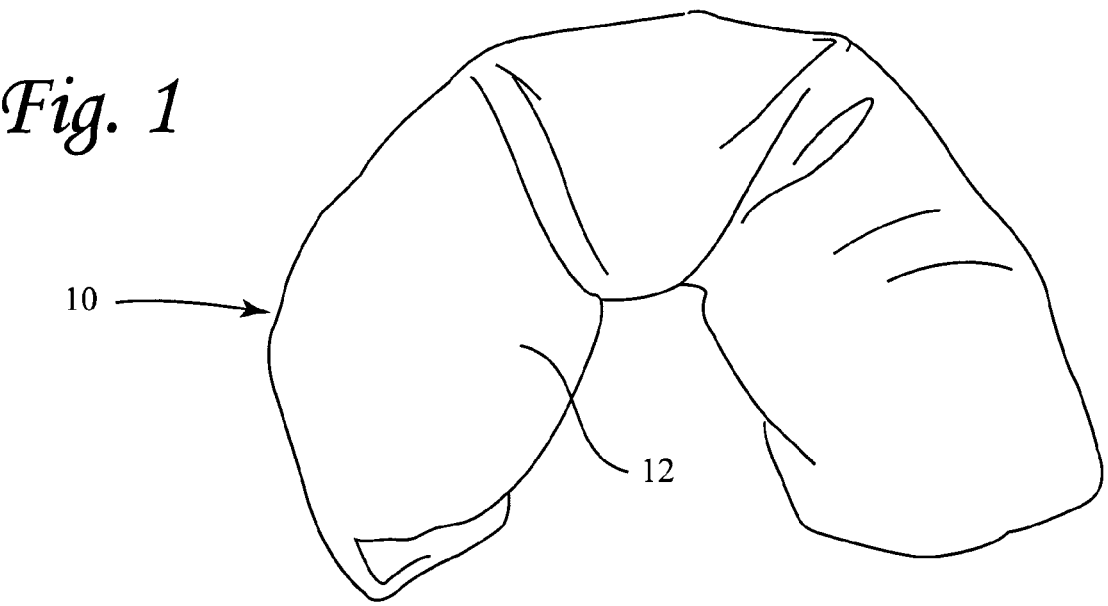
Referring to FIG. 1, a perspective view of the therapeutic pillow 10 of this invention.
Figure 2:
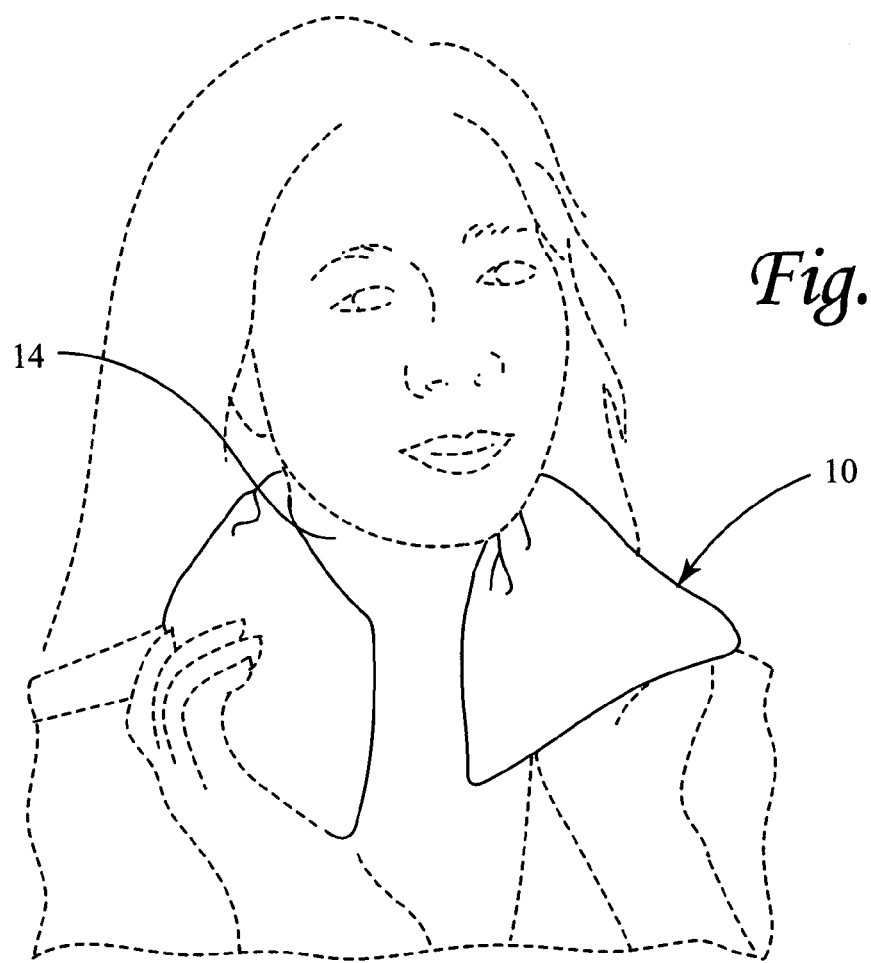
FIG. 2 is a perspective view of the therapeutic pillow of FIG. 1 shown placed on the neck of a user to relieve hot flashes.

Referring to FIG. 1 is a perspective view of the therapeutic pillow 10 of this invention. It is flexible, and has an outer sleeve cover 12 formed from soft cotton and bears a color or pattern as desired. The pillow is kept in the freezer compartment of a refrigerator so it is ready to use when needed, such as when one is disturbed by hot flashes, night sweats, an overheated body, insomnia, menopausal or perimenopausal symptoms, or andropause in men. As shown in FIG. 2, the therapeutic pillow is draped over the neck of a user 14 on the stellate-ganglion area of the neck to relieve hot flashes and the like.

The cooled pillow can be used while sitting, standing, walking, or lying down. It contains filler that is chosen to have sufficient weight and flow properties to provide a comforting wrapping effect on the back of the neck and feels exquisitely comfortable when applied directly on bare skin. It requires no preparation, just storing in a freezer prior to use. Because of the nature of its filler can fold in half to save freezer space. It has a machine washable outer sleeve, is easily portable and made to last.

Figure 3:
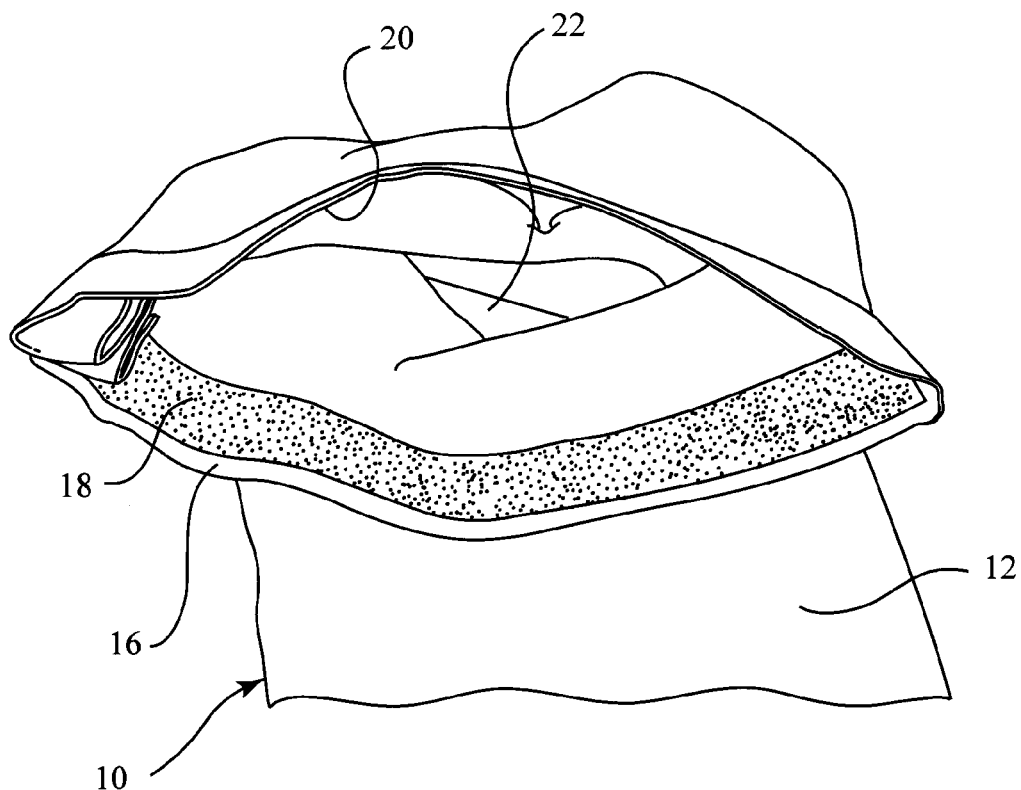
FIG. 3 is a view of the open end of the outer sleeve of the pillow of FIG. 1 showing the end of an inner sleeve inserted therein.

FIG. 3 is a view of the open end 16 of the outer sleeve 12. The outer sleeve 12 is made of soft cotton and can bear a decorative design. It is fitted with opposing hook and loop Velcro strips 18 and 20 sewn to the inner edge surfaces of the open end 16. A portion is shown of the end of an inner sleeve 22 inserted into the outer sleeve 12, which is about the same size as the inner sleeve 22. After the inner sleeve 22 is filled and closed and slid into the outer sleeve 12, the outer sleeve 12 is closed by "zipping" the Velcro strips 18 to form the pillow 10.

Figure 4:
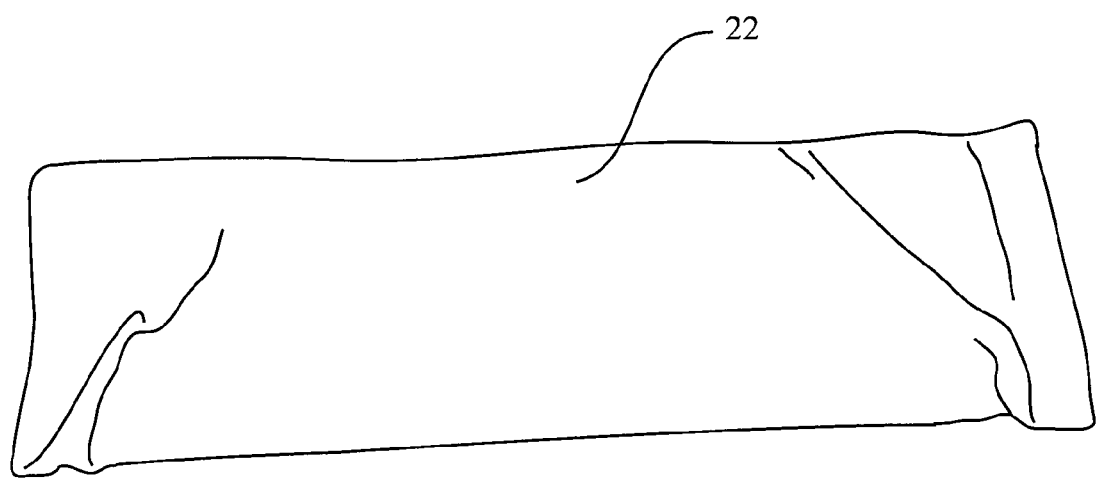
FIG. 4 is a perspective view of the filled inner sleeve of the pillow of FIG. 1 and partially shown in FIG. 3.
Figure 5:
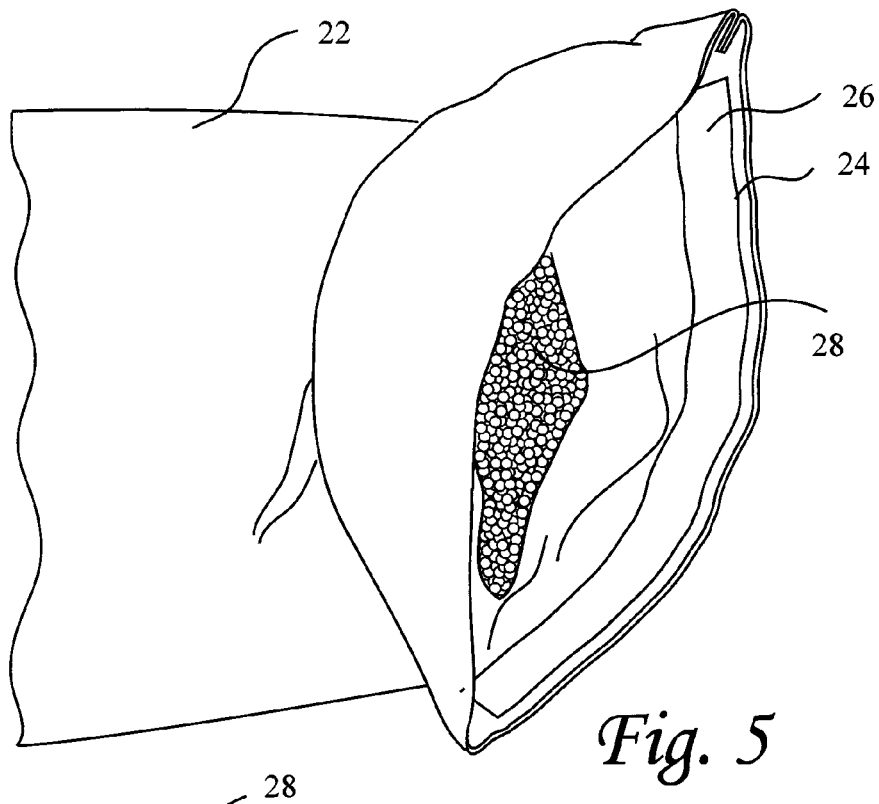
FIG. 5 is a view of the open end of the inner sleeve of FIG. 4 and showing wheat berries therein.

FIG. 4 shows the filled inner sleeve 22. The inner sleeve 22 is made of muslin, such as is formed from unbleached or white cloth produced form carded cotton yarn. FIG. 5 is a view of the open end 24 of the inner sleeve 22. It is fitted with opposing hook and loop Velcro strips, one of which is shown at 26, sewn to the inner edge surfaces of the open end 24. A portion of wheat berries 28 is shown inside the inner sleeve 24. The inner and outer sleeves 12 and 22 are each about 18 inches long, 5½ inches wide and 1½ inches thick. The inner sleeve 22 contains 2½ pounds of the wheat berries 28, which together with the dimensions of the inner and outer sleeves, has sufficient weight and flow properties to provide a comforting wrapping effect on the back of the neck.

Figure 6:
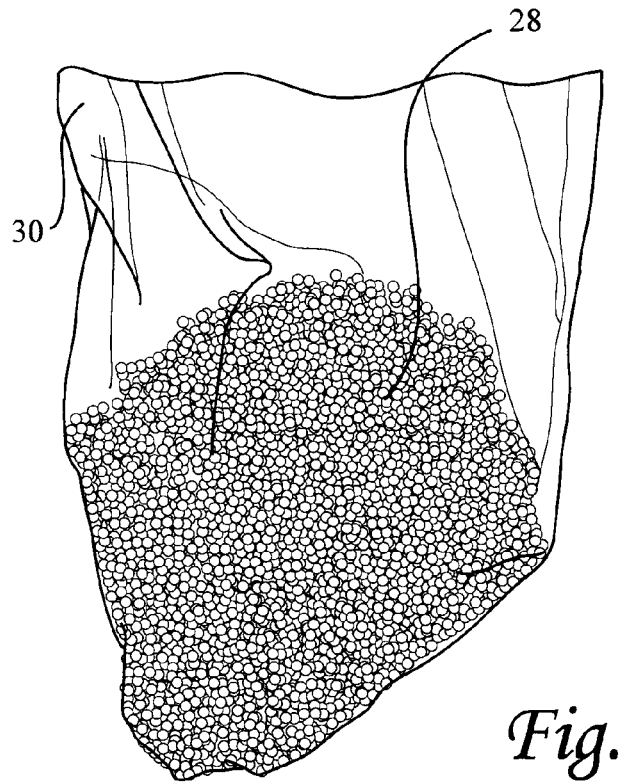
FIG. 6 shows wheat berries that are used to fill the inner sleeve of FIG. 4 as partially shown in FIG. 5

FIG. 6 shows the 2½ pounds of wheat berries 28 measured out in a container 30 used to fill the inner sleeve. The wheat berries, also referred to as wheatberries, are reddish, raw, natural whole grains composed of its bran, germ, and endosperm. The inner sleeve 22 is filled with the wheat berries and closed and slid into the outer sleeve 12. The outer sleeve 12 is closed by "zipping" the Velcro strips 18 to form the pillow 10.

Figure 7:
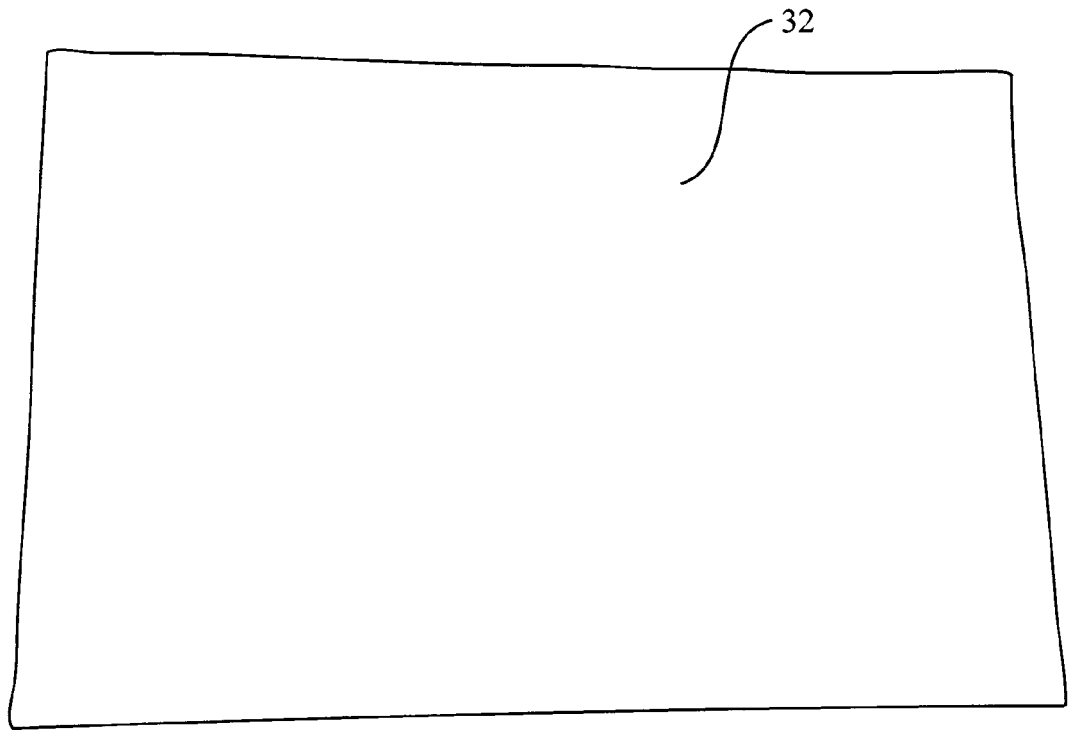
FIG. 7 is a planar view of a sheet of muslin used to form the inner sleeve.
Figure 8:
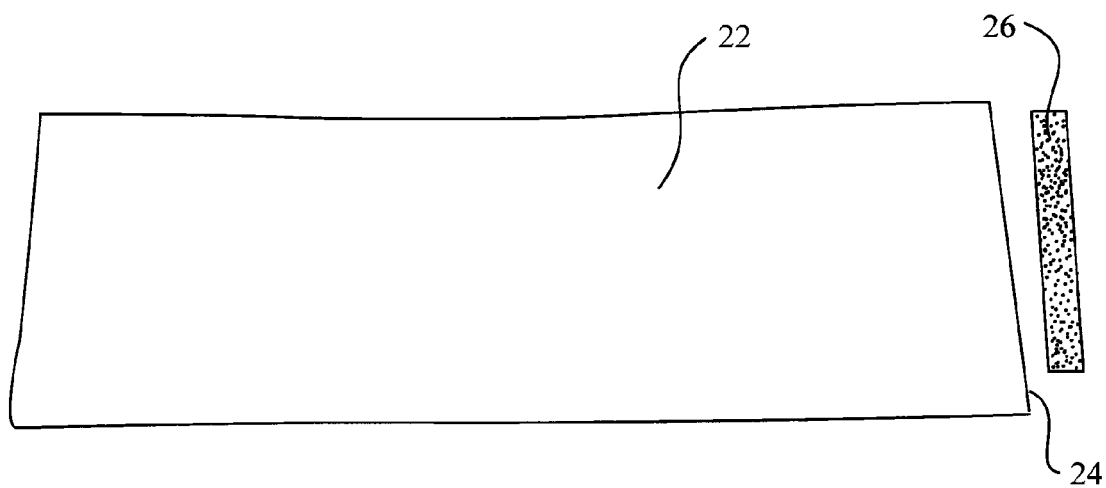
FIG. 8 is a planar view of the sheet of muslin of FIG. 7 folded in preparation for sewing one end and the elongate edge.

The inner sleeve 22 is constructed from a sheet of muslin 32 shown in FIG. 7, which is folded over as shown in FIG. 8. The folded sheet is sewn along its left and top edges to form the elongate inner sleeve 22. Velcro strips, one of which 18 is shown, is sewed to the inner edges of the open end 24 of the sleeve 22. Muslin is formed from unbleached or white cloth produced form carded cotton yarn, and provides a strong container when the Velcro strips are "zipped" together.

Figure 9:
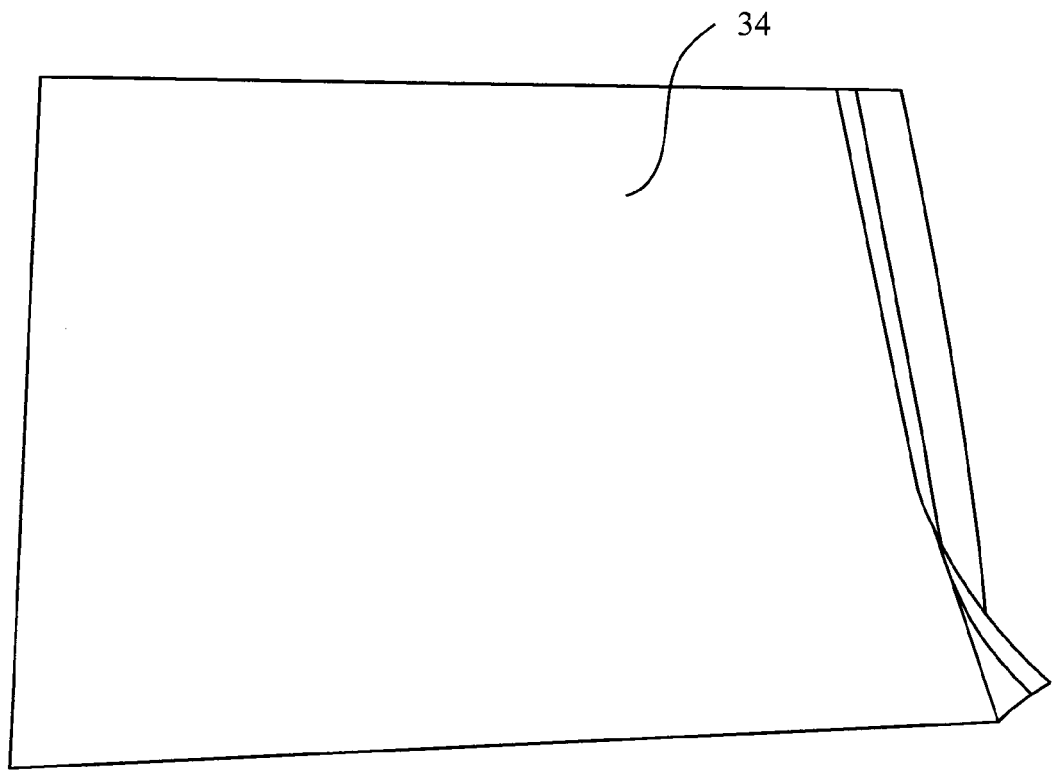
FIG. 9 is a planar, partially perspective, view of a sheet of soft cotton used to form the outer sleeve of the pillow.
Figure 10:
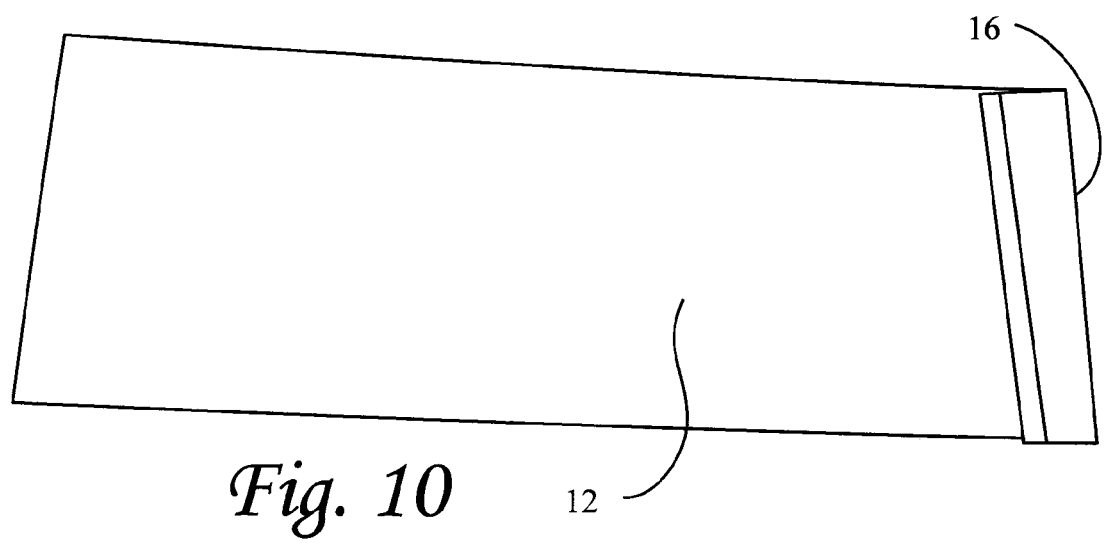
FIG. 10 is a planar view of the sheet of soft cotton of FIG. 9 folded in preparation for sewing one end and the elongate edge.

The outer sleeve 12 is constructed from a sheet of soft cotton 34 to enable it to have a soft feel to the skin. It can be decorated with a pattern, design or logographic. The cotton sheet 34 forming the outer sleeve is shown in FIG. 9, which is folded over as shown in FIG. 10. As with the inner sleeve 22, the material 34 for the outer sleeve 12 is sewn along its left and top edges to form the elongate outer sleeve 22. Velcro strips, one of which 26 is shown, is sewed to the inner edges of the open end 16 of the sleeve 22.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

The invention claimed is:

1. An apparatus for applying to a person's neck in need for relief from hot flashes or body overheating or insomnia, said apparatus consisting of:

an elongate flexible and bendable pillow filled with raw natural whole grains composed of bran, germ, and endosperm as filler to provide a conformation wherein the opposite ends of said pillow are filled with said filler and directly face each other whereby the pillow is self-supporting on the person's neck to wrap around the person's neck to provide a comforting wrapping effect on a stellate-ganglion area of the person's neck and, said pillow having a single elongate inner compartment formed of muslin enclosed in and filling entirely a single elongate outer compartment, said pillowing having a length to width ratio of about 3.3, the single elongate inner compartment being formed as a sleeve with a closable opening at one end to receive the filler, the single elongate outer compartment being formed as a sleeve with a closable opening at one end to receive the elongate inner compartment, whereby the combination consisting of the pillow's said conformation, its dimensions, its single elongate inner compartment, its single elongate outer compartment, and its filler solely enable the pillow to be self-retained on the person's neck.

2. The apparatus of claim 1 where the single elongate inner compartment and the single elongate outer compartment are each about 18 inches long; 5½ inches wide and 1½ inches thick, and wherein the inner compartment contains 2½ pounds of said whole grains comprising wheat berries.

3. The apparatus of claim 1 wherein said raw, natural whole grains are wheat berries.

4. The apparatus of claim 1 including opposing hook and loop strips on the opening of the elongate inner compartment for closing said opening of the elongate inner compartment, and including opposing hook and loop strips on the opening of the elongate outer compartment for closing said opening of the elongate outer compartment.

\* \* \* \* \*